US009879220B2

United States Patent
Wang et al.

(10) Patent No.: US 9,879,220 B2
(45) Date of Patent: Jan. 30, 2018

(54) DUPLEX REACTOR SYSTEM FOR REMOVAL OF TEBUCONAZOLE AND METHOD THEREOF

(71) Applicants: Nanjing University, Nanjing (CN); Nanjing University Yancheng Environmental Protection Technology and Engineering Research Institute, Yancheng (CN)

(72) Inventors: Jinnan Wang, Nanjing (CN); Chen Chen, Nanjing (CN); Dadao Wang, Nanjing (CN); Shuyan Tian, Nanjing (CN)

(73) Assignee: Beijing University of Technology, Beijing (CN)

( * ) Notice: Subject to any disclaimer, the term of this patent is extended or adjusted under 35 U.S.C. 154(b) by 0 days.

(21) Appl. No.: 15/114,225

(22) PCT Filed: Jul. 13, 2015

(86) PCT No.: PCT/CN2015/083877
§ 371 (c)(1),
(2) Date: Jul. 26, 2016

(87) PCT Pub. No.: WO2016/041403
PCT Pub. Date: Mar. 24, 2016

(65) Prior Publication Data
US 2016/0347636 A1    Dec. 1, 2016

(30) Foreign Application Priority Data

Sep. 19, 2014 (CN) .......................... 2014 1 0484704

(51) Int. Cl.
*C02F 3/00* (2006.01)
*B01D 15/00* (2006.01)
(Continued)

(52) U.S. Cl.
CPC .................. *C12N 1/20* (2013.01); *C02F 3/06* (2013.01); *C02F 3/341* (2013.01); *C02F 1/285* (2013.01);
(Continued)

(58) Field of Classification Search
CPC .. Y02W 10/15; C02F 3/06; C02F 3/10; C02F 3/101; C12M 25/18
(Continued)

(56) References Cited

U.S. PATENT DOCUMENTS 5,403,487 A     4/1995 Lodaya et al.
2012/0138527 A1*  6/2012 Ren ...................... C02F 3/2806
                                                     210/603

FOREIGN PATENT DOCUMENTS

CN    101613131 A    12/2009
CN    102923919 A    2/2013
(Continued)

*Primary Examiner* — Claire A Norris (57) ABSTRACT

Implementations herein relate to systems and methods for removal of tebuconazole from water using a duplex reactor. Water samples containing tebuconazole enter a double sandwich of the duplex reactor, and then enter a reactor inner shell of the duplex reactor through a water distributor. In the duplex reactor, the tebuconazole is removed by adsorption resins loaded with microorganisms. After the removal, a concentration of the tebuconazole in adsorption effluent is below the standard limit of the national pesticide wastewater discharge. The microorganisms loaded on the resins use organic carbon (e.g., tebuconazole) in water as a carbon source and degrade tebuconazole that is absorbed by the resins. The systems and methods not only solve problems associated with conventional techniques (e.g., poor water quality fluctuations and lacking of time long degradation), but also address issues associated with resin adsorption methods (e.g., secondary pollution derived from resins regeneration).

9 Claims, 4 Drawing Sheets

(51) Int. Cl.
- *C12N 1/20* (2006.01)
- *C02F 3/06* (2006.01)
- *C02F 3/34* (2006.01)
- C02F 1/28 (2006.01)
- C02F 3/10 (2006.01)
- C02F 101/30 (2006.01)

(52) U.S. Cl.
CPC ........ *C02F 3/108* (2013.01); *C02F 2101/306* (2013.01); *C02F 2209/40* (2013.01); *C02F 2303/16* (2013.01); *C02F 2305/06* (2013.01); *Y02W 10/15* (2015.05)

(58) Field of Classification Search
USPC ................ 210/150, 610, 615, 620, 188, 263
See application file for complete search history.

(56) References Cited

FOREIGN PATENT DOCUMENTS

| | | |
|---|---|---|
| CN | 203187462 U | 9/2013 |
| CN | 103951031 A | 7/2014 |
| CN | 104030438 A | 9/2014 |
| JP | 2001300571 A | 10/2001 |
| JP | 2002017843 A | 1/2002 |

\* cited by examiner

DUPLEX REACTOR SYSTEM FOR REMOVAL OF TEBUCONAZOLE AND METHOD THEREOF

CROSS REFERENCE TO RELATED APPLICATION

This application is a national stage application of international application number PCT/CN2015/083877, filed Jul. 13, 2015, titled "Duplex Reactor System for Removal of Tebuconazole and Method thereof," which claims the priority benefit of Chinese Patent Application No. 201410484704.0, filed on Sep. 19, 2014, which is hereby incorporated by reference in its entirety.

TECHNICAL FIELD

Implementations herein relate to systems and methods for removal of tebuconazole, more particularly to systems and methods for removal of tebuconazole in water using a duplex reactor including resins loaded with microorganisms.

BACKGROUND

Pesticides play an important role in controlling agricultural pests and diseases as well as in increasing crop yields. However, the agricultural industry increasingly depends on pesticides, which contaminate soil and water. For example, merely 0.3% of pesticides work on pests, and the remaining 99.7% of pesticides are left on surfaces of crops and in the natural environment including soil and water. Eventually, these pesticides enter rivers, lakes and groundwater through rainfall and irrigation. This results in potential health hazards to humans and other aquatic organisms. Tebuconazole is an important pesticide and widely used in the world. Tebuconazole effectively controls various agricultural diseases such as rust, powdery mildew, net blotch, root rot, *Fusarium* head blight and smut associated with crops as well as rust, powdery mildew and scab, and other fungal diseases associated with fruits. Currently, tebuconazole has been registered on 65 kinds of crops in more than 50 countries; therefore, related environmental problems are increasingly urgent. Although tebuconazole concentrations in the environment are not high, potential hazards and risks of tebuconazole to the environment cannot be ignored. Therefore, many scholars have studied treatment of tebuconazole in wastewater, and several methods for removal of tebuconazole have been reported. Generally, these methods can be categorized into three main categories.

The first category includes a biochemical-based method, which utilizes microorganism organisms to break tebuconazole structures and turn these structures into small molecules that are less toxic and/or susceptible to be degraded. Although the method is economically applicable, the method has the following disadvantages: (1) Anti-water quality fluctuation capability is weak, and the method cannot afford charges from high pollution loads in wastewater; (2) Microbial degradation of tebuconazole (e.g., taking 3-5 days) is slower than that of conventional techniques such as adsorption and chemical oxidation based methods. Although it has been reported of strains capable of screening and degrading tebuconazole (Hongping Wu et al., Tebuconazole pesticide screening degrading bacteria and their degradation of performance, pesticide, Feb. 2013 10). However, Hongping Wu et al. does not identify the type of bacteria for removal of tebuconazole, provides no embodiments using the strains as well as systems implementing the method. Therefore, methods for removal of tebuconazole using biodegradable techniques have not been reported.

The second category includes an adsorption-based method, which separates tebuconazole from water without altering its chemical structure. Although the absorption-based method is the most common and more efficient approach in the laboratory or the industry, this method has a serious problem: desorption solutions for resin regeneration. Thus, effective desorption disposals have to be used; otherwise secondary pollution will happen. Currently, research has been focused on the adsorption method implementing activated carbon on adsorption of tebuconazole; however, implementations of resin adsorption techniques to remove tebuconazole from wastewater has not been reported.

The third category includes a chemical-oxidation-based method, which implements chemical-oxidation processes to remove tebuconazole from water. This method has been patented (e.g., An immobilized microorganism treatment of organic phosphorus pesticide wastewater use, Publication Number: CN103102015A). However, this method requires adding more chemical agents, involves complex operations, and incurs high operating costs. Further, this method is not efficient and economically applicable to remove tebuconazole in a low concentration from wastewater. In addition to adding excessive chemical agents, the method may further deteriorate quality of water and increase toxicity of water.

To overcome these disadvantages, there is a need for developing systems and methods for efficiently remove tebuconazole in water.

SUMMARY

Technical Problems to be Solved

To solve the problems with existing techniques for removal of tebuconazole in water, implementations herein provide systems and methods for removal of tebuconazole in water using resins loaded with microorganisms. The implementations adopt a new type of adsorption resins loaded with microorganisms as adsorption fillers filled into a duplex reactor. The duplex reactor is able to rapidly adsorb and remove tebuconazole in water, and then degrades tebuconazole adsorbed on the resins to regenerate the resins.

There are techniques related to wastewater treatments including oxidation, bio-degradation and adsorption based techniques. But these techniques are not suitable for removal tebuconazole removal from water. For example, although these techniques have advantages in pesticide wastewater treatment, they have deficiencies, which are provided below.

(1) Comparison between the implementations herein and existing techniques based on oxidation processes (e.g., Patent 1: Tebuconazole pesticide wastewater treatment, CN Patent NO. 102923919 A). This technique degrades tebuconazole using processes associated with Fenton oxidation, oxidation using chlorine dioxide, iron and carbon-coagulation integrated oxidation. However, there are some problems with removal of tebuconazole using this technique.

For example, the process requires pH adjustment, consumes large amounts of acid. Also, large amounts of sludge and sediment are produced during the Fenton oxidation of iron and carbon-coagulating sedimentation process. Such substances are hazardous wastes and require safe disposals, which incur higher costs. This technique is usually used for high concentration wastewater treatment; however, it cannot efficiently remove contaminants (e.g., tebuconazole) in low concentrations from water. Therefore, the technique is not economically applicable. Further, disposal of a large number of chemical wastes severely alter quality of water and fail to make balance and protection of water ecosystems.

(2) Comparison between the implementations herein and existing techniques based on biodegradable processes (e.g., Patent 2: A use of immobilized microorganism method of governance organophosphorus pesticide wastewater, CN Patent Publication No: CN103102015A). For example, domesticated fungus (e.g., *Aspergillus Niger*) was adsorbed onto activated carbon with a diameter of 5-8 mml, and the obtained saturated activated carbon containing *Aspergillus Niger* was placed into waste water to degrade organophosphorus pesticides. However, there are problems for removal of tebuconazole. *Aspergillus Niger* can only degrade organophosphorus pesticides and is not able to degrade tebuconazole. Activated carbon has mainly microporous structures, which have small adsorption capacity and low adsorption rates. Also, *Aspergillus Niger* causes clogged pores due to adhesion and adsorption are hardly performed. The active carbon only functions as a carrier of the bacteria; there are no supporting reactor and processing systems. After placing into water, the active carton may be not separated from the water, having difficulties in practical application.

(3) Comparison between the implementations herein and existing techniques based on adsorption processes (e.g., Patent 3: A pesticide industrial wastewater treatment, CN Patent Publication No: CN101746930 A). The techniques include aerobic biological treatment of wastewater using continuous adsorption between wastewater containing quinolone parathion and magnetic resins. Further the technique uses a suspended bed up flow reactor as magnetic resins to contact adsorption reactors and allow continuous access to water such as to adsorb and remove contaminants from the water. However, the technique has disadvantages. The magnetic resins remove contaminants through ion exchange; however, tebuconazole in water is not ionized. Thus, tebuconazole cannot be removed by ion exchange processes. Further, after adsorption of pollutants, the magnetic resins have to be regenerated using brine as renewable liquid; therefore, disposal processes of the renewable liquid may produce secondary pollution.

Technical Solutions

The implementations relate to a duplex reactor including multiple layers of resins to remove tebuconazole and to degrading of the tebuconazole adsorbed on the resins using microorganisms loading on the resins such that the resins are regenerated and continuous water inlet and outlet are achieved.

As compared with existing techniques, the implementations have the following features and/or advantages.

(1) Using polymer resin absorbent materials as microorganism carriers. These resins not only are loaded with microorganisms, but also are capable of adsorbing tebuconazole in water. Adsorption capacity and adsorption rates are high.

(2) Loading the resins with microorganisms such as *Sphingomonas paucimobilis* (e.g., *Sphingomonas* sp.). The microorganisms have a good degradation capacity of tebuconazole, and absorbed resins may be regenerated without additional desorption solutions. Accordingly, removal of tebuconazole does not change water quality and produces no additional desorption and liquid waste.

(3) New duplex structure and multilayer adsorption materials of the duplex reactor. The duplex reactor effectively increases contacting time among adsorbent materials, microorganisms, and contaminants to improve an adsorption removal rate and a bio-degradation rate associated with tebuconazole in water.

(4) Multi-cellular polymer support frame in the duplex reactor. The duplex reactor effective reduces swelling and accumulation of pressure among adsorbent materials to avoid fragmentation and loss of the adsorbent materials, meanwhile to avoid compaction and clogging by reducing a size of monolayer stories of adsorbent materials.

The implementations relate to a duplex reactor for removal of tebuconazole from water. The duplex reactor includes a reactor shell, a reactor inner shell, an inlet pipe, a water distributor, an outlet pipe, an aeration tube, an aeration head, an exhaust pipes, a gas gathering reflective cone, a honeycomb support frame, resins loaded with microorganisms, a backwash water inlet, a backwash water outlet pipe. In some implementations, the inlet pipe is located at the top of the duplex reactor, which is connected to the reactor shell; the exhaust pipe is in the vicinity of a conical collection hood and connected to the reactor inner shell; the outlet pipe is located in the upper part of the reactor, located in the lower part of the conical collection hood, and connected to the reactor inner shell; the honeycomb support frame is located in the reactor inner shell, which is filled with the resins loaded with microorganisms; the water distributor is located at the bottom of the reactor inner shell; the backwash water outlet pipe is above in each layer of the honeycomb support frame and connected to the reactor inner shell; the backwash water inlet pipe is located at the bottom of the water distributor and is connected to the reactor shell; the aeration tube is connected to the aeration head, and the aeration head is located directly above the reactor water distributor.

Implementations herein relate to systems and methods for removal of tebuconazole in water using resins loaded with microorganisms. The system includes the duplex reactor, a complementary nutrient solution reserve tank, an inlet water sample adjustment tank, a backwash effluent collection tank, a backwash water reserve tank, a filter, a flow meter, a pump and an aeration pump, wherein the complementary nutrient solution reserve tank and the inlet adjustment tank are connected, the duplex reactor is connected to the inlet water sample adjustment tank, the backwash water reserve tank, the backwash effluent collection tank, and the aeration pump.

Implementations herein relate to a method for removal of tebuconazole in water using resins loaded with microorganisms using the duplex reactor.

Figure 1:
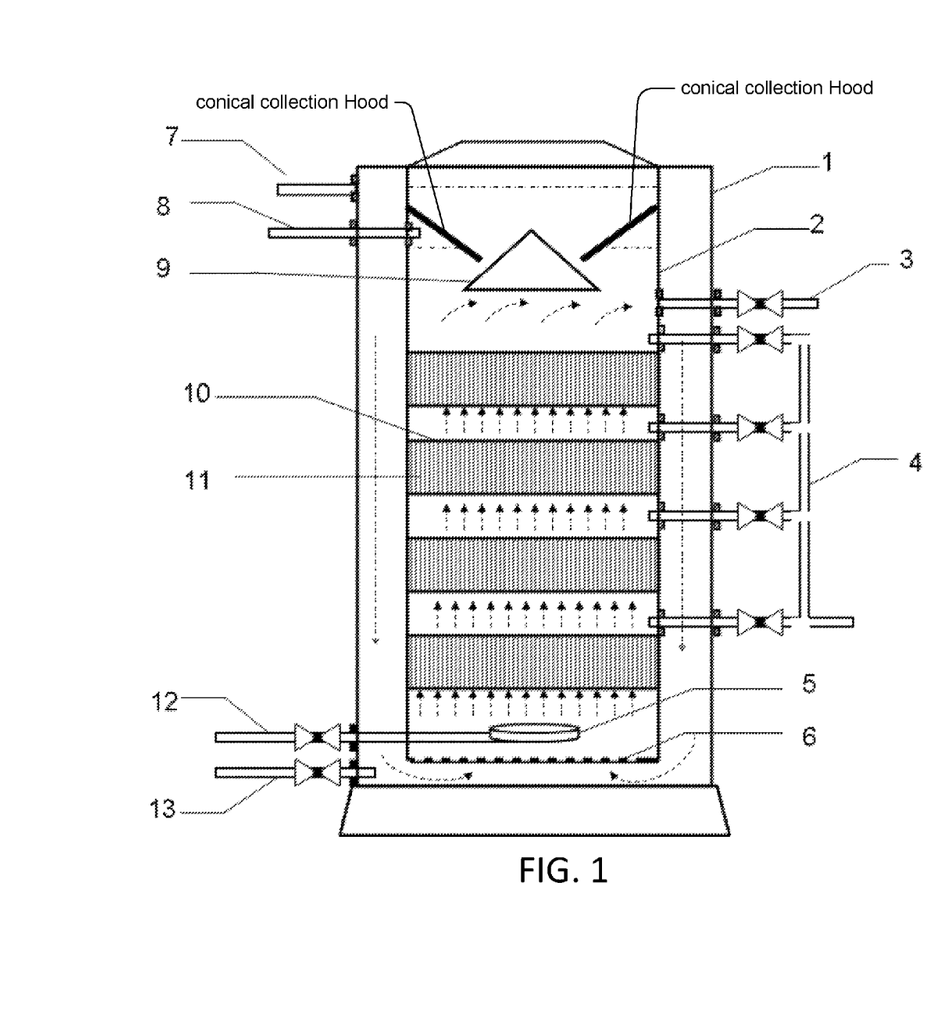
Figure 2:
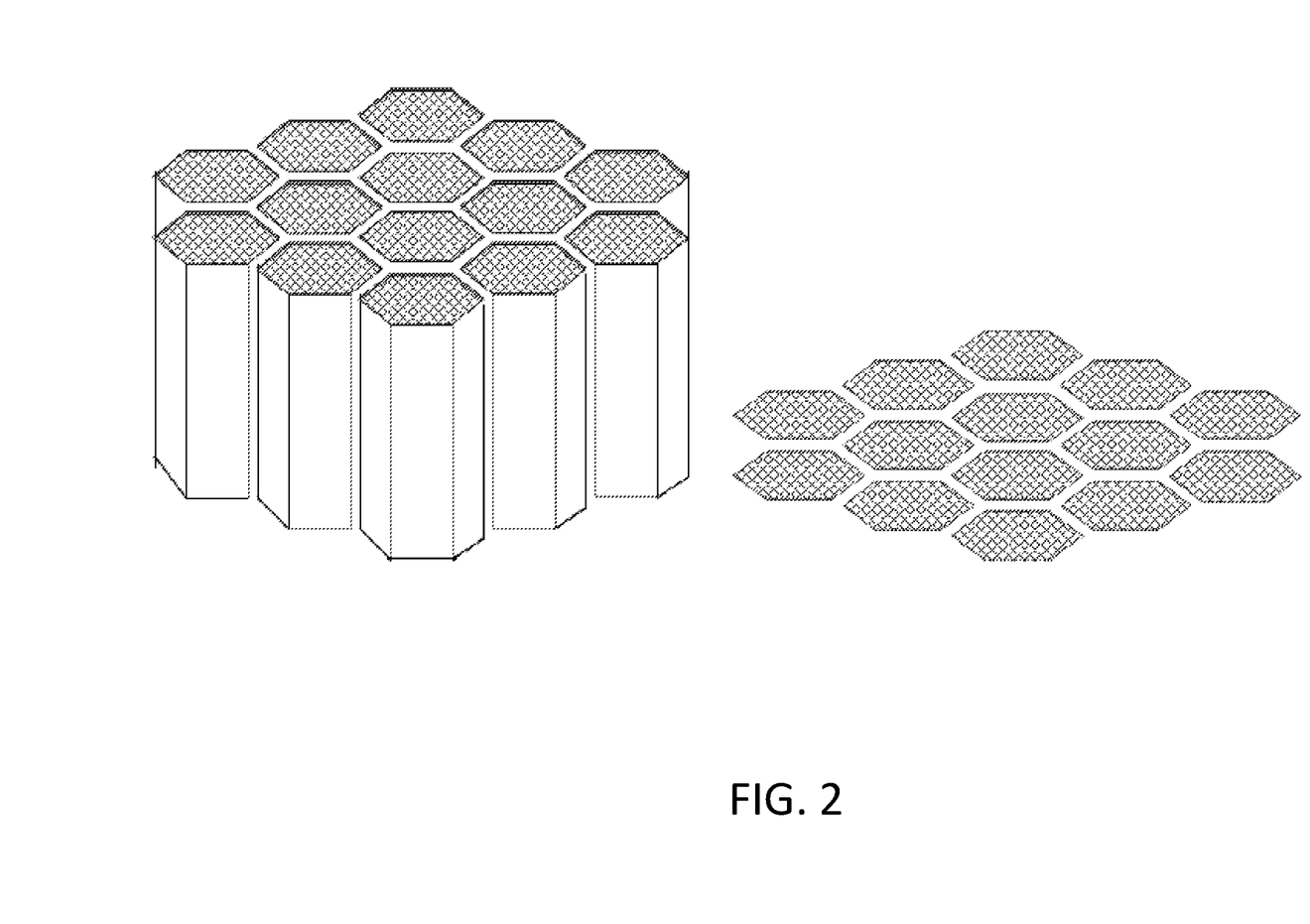
Figure 3:
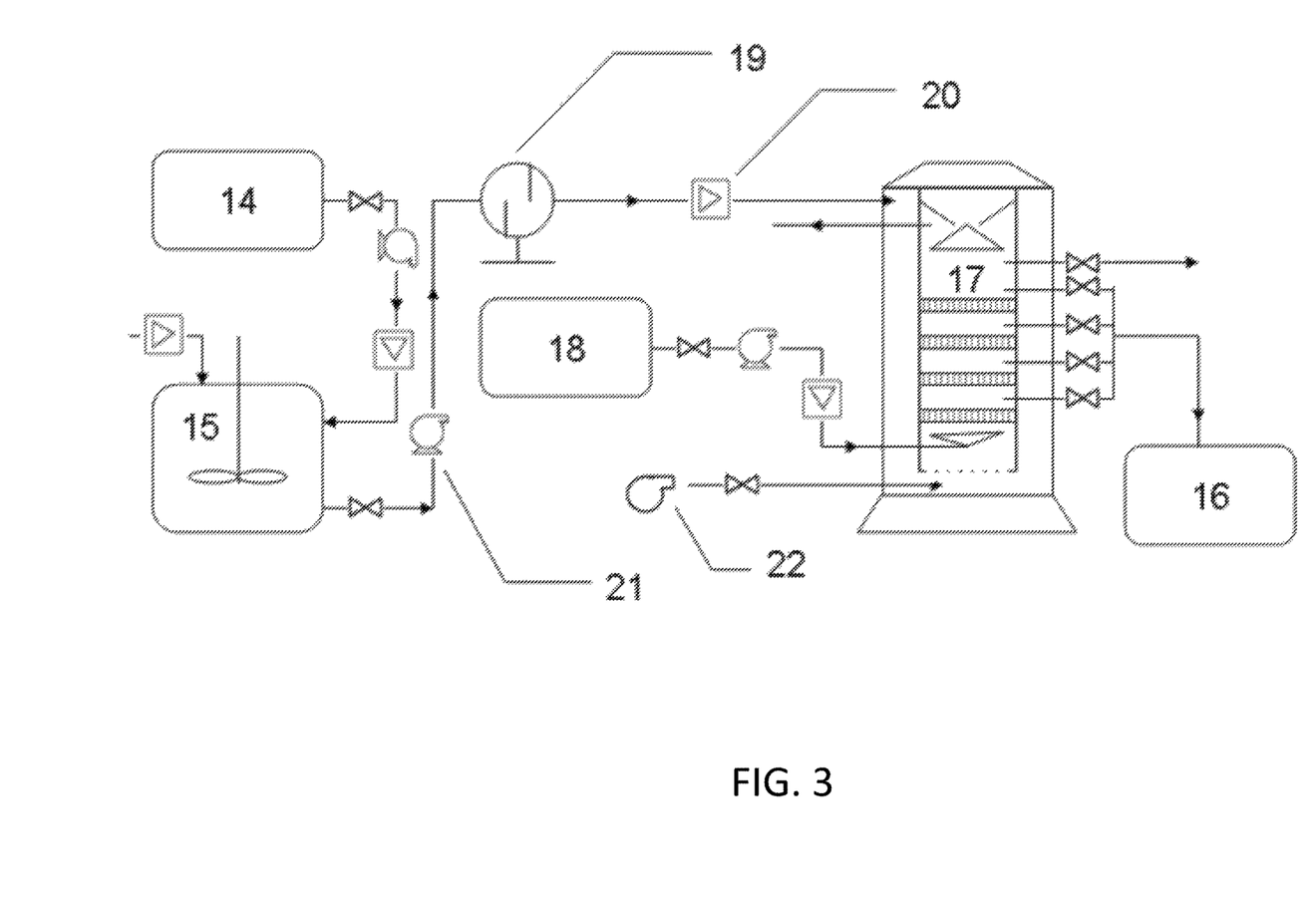

Step 1. Providing the resins loaded with microorganisms:

(a) Culturing microorganisms by: inoculating *Sphingomonas* bacterium colonies from plates (*Sphingomonas* sp. was isolated from soil. In 1990, Japanese scholars Yabuuchi first proposed *Sphingomonas paucimobilis*. Takeuchi et al. made changes in 1993. According to 16S rRNA sequence comparison, *Sphingomonas paucimobilis* belongs to 4 subclass of proteobacteria. The strain of the genus is Gram-negative bacteria, has no spores, shows unilateral born polar flagellar motility, is mostly yellow, is obligate aerobic and produces catalase) into culture media including beef peptone and keeping the culture media from light at temperature 28 degrees Celsius;

(b) Collecting microorganisms: separating the *Sphingomonas paucimobilis* at a logarithmic growth phase from the culture media by centrifugation for 20 min with a speed of 5000 G. Washing the *Sphingomonas* bacteria using a solution (pH=7.3) containing disodium hydrogen phosphate and potassium dihydrogen phosphate;

(c) Loading the microorganisms to the resins: placing the collected *Sphingomonas paucimobilis* into culture media containing minerals, adding the resins to the culture media containing minerals, and shaking the culture media containing minerals for 3-5 days to obtain the resins loaded with *Sphingomonas paucimobilis*; and (d) Filling in the resins: washing the resins loaded with microorganisms using deionized water, and filling the resins into the double honeycomb support frame of the duplex reactor. The used strains are *Sphingomonas paucimobilis* (*Sphingomonas* sp.), and the resins are adsorption resins with a polystyrene backbone or a polyacrylate backbone.

Step 2. Adding water: adjusting water flow and flow of the complementary nutrient solution, controlling the inlet water sample adjustment tank such that CODCr of water samples is not less than 20 mg/L, allowing the water samples into the inlet pipe of the duplex reactor, and opening the aeration pump. the complementary nutrient solution may include methanol, ethanol, glucose, or a solution of sodium acetate.

Step 3. Adsorption and bio-degradation of tebuconazole: allowing the water samples pass through multiple layers of the resins, removing tebuconazole by the resin, and discharging adsorption water from the outlet pipe, wherein, at the same time, microorganisms attached to the resins use complementary nutrients, and tebuconazole are used as a carbon source such as to degrade the tebuconazole, and the water samples are kept in the duplex reactor for at least 30 minutes.

Step 4. Backwash: 7-10 days after the bio-degradation, due to the situation that attached microorganisms metabolism on the resins result in death and loss of certain microorganisms, closing the feed line pumps, valves and outlet valves, opening valves of the backwash water inlet and the backwash water outlet pipe, backwashing the resins for not less than two minutes, placing the backwash water into the backwash water effluent collection tank, discharging the backwash water into a sewage treatment plant, closing the valves of the backwash water inlet pipe and backwash water inlet outlet pipe, opening the valve and the pump of the inlet water pipeline, the water inlet valve, and continuing to run operations.

Beneficial Effects (1) The duplex reactor is capable of water collection, water distribution, aeration, exhaust, adsorption, bio-degradation, backwash and other functions and therefore is capable of continuously running. The duplex further has a small size but high efficiency for removal of tebuconazole.

(2) Multi-layer honeycomb support frame and filtering screens can reduce pressure caused by excessive accumulation of resin layers and avoid a situation that the resin layers in water swell and cause enormous pressure and crushing loss. The structure further avoids increase of water resistance caused by hardening of whole resin layers. This reduces head loss and saves power consumption.

(3) *Sphingomonas paucimobilis* (*Sphingomonas* sp.) loaded on the resins effectively adsorbs tebuconazole. And the adsorption capacity and adsorption rate are high, and removal of tebuconazole takes place without changing water quality.

(4) Adsorbed resins do not have to be transferred. There is no need of regeneration using decorbent solutions. *Sphingomonas paucimobilis* (*Sphingomonas* sp.) loaded on the resins degrades tebuconazole that are absorbed by the resins to achieve resin regeneration without incurring desorption solutions.

BRIEF DESCRIPTION OF THE DRAWINGS

FIG. 1 is a schematic diagram illustrating a duplex reactor in accordance with the implementations of the present disclosure. As illustrated, 1 refers to a reactor shell; 2 refers to a reactor inner shell; 3 refers to an outlet pipe of the reactor; 4 refers to a backwash water outlet pipe; 5 refers to an aeration head; 6 refers to a water distributor; 7 refers to an inlet pipe; 8 refers to an exhaust pipe; 9 refers to a gas gathering reflective cone; 10 refers to a honeycomb support frame; 11 refers to a resins loaded with microorganisms; 12 refers to an aeration tube; and 13 refers to a backwash water inlet pipe.

FIG. 2 is a schematic diagram illustrate a honeycomb support frame (support frame, internal filtering screens) of a duplex reactor in accordance with the implementations of the present disclosure, the left part of the diagram indicates a wall of the support frame, the right part of the diagram shows the support frame and the top portion of the bottom of the filtering screen, which prevents the resins to be washed away.

FIG. 3 is a schematic diagram illustrating a system structure in accordance with the implementations of the present disclosure. As illustrated, 14 refers to a complementary nutrient solution reserve tank; 15 refers to a regulate water tank; 16 refers to a backwash water effluent collection tank; 17 refers to a duplex reactor; 18 refers to a backwash water storage tank; 19 refers to a filter; 20 refers to a flow meter; 21 refers to a pump; and 22 refers to an aeration pump.

FIG. 4 is a flow chart illustrating a process in accordance with the implementations of the present disclosure.

DETAILED DESCRIPTION OF THE PREFERRED EMBODIMENTS

The present disclosure is further explained below by examples.

Example 1

An architecture of a system for processing wastewater is shown in FIG. 3, and the architecture includes: a duplex reactor (17), a complementary nutrient solution reserve tank (14), an inlet water sample adjustment tank (15), a backwash effluent collection tank (16), a backwash water reserve tank (18), a filter (19), a flow meter (20), a pump (21) and an aeration pump (22), wherein the complementary nutrient solution reserve tank (14) and the inlet adjustment tank (15) are connected, the duplex reactor (17) is connected to the inlet water sample adjustment tank (15), the backwash water reserve tank (18), the backwash effluent collection tank (16), and the aeration pump (22); the duplex reactor (17) is connected to the inlet water sample adjustment tank (15), between which there are the backwash water reserve tank (18), the backwash effluent collection tank (16), and the aeration pump (22).

As illustrated in FIG. 1, the duplex reactor (17) include includes: a reactor shell (1), a reactor inner shell (2), an inlet pipe (7), a water distributor (6), an outlet pipe (3), an aeration tube (12), an aeration head (5), an exhaust pipe (8), a gas gathering reflective cone (9), a honeycomb support frame (10), resins loaded with microorganisms (11), a backwash water inlet pipe (13), a backwash water outlet pipe (4); wherein the inlet pipe is (7) located at the top of the duplex reactor, which is connected to the reactor shell (1); the exhaust pipe (8) is in the vicinity of a conical collection hood and connected to the reactor inner shell (2); the outlet pipe (3) is located in the upper part of the reactor, located in the lower part of the conical collection hood, and connected to the reactor inner shell (2). As illustrated in FIG. 2, the honeycomb support frame (10) is located in the reactor inner shell 2, which is filled with the resins loaded with microorganisms (11); the water distributor (6) is located at the bottom of the reactor inner shell (2); the backwash water outlet pipe (4) is above in each layer of the honeycomb support frame (10) and connected to the reactor inner shell (2); the backwash water inlet pipe (13) is located at the bottom of the water distributor (6) and is connected to the reactor shell; the aeration tube (12) is connected to the aeration head (5), and the aeration head (5) is located directly above the reactor water distributor (6).

Figure 4:
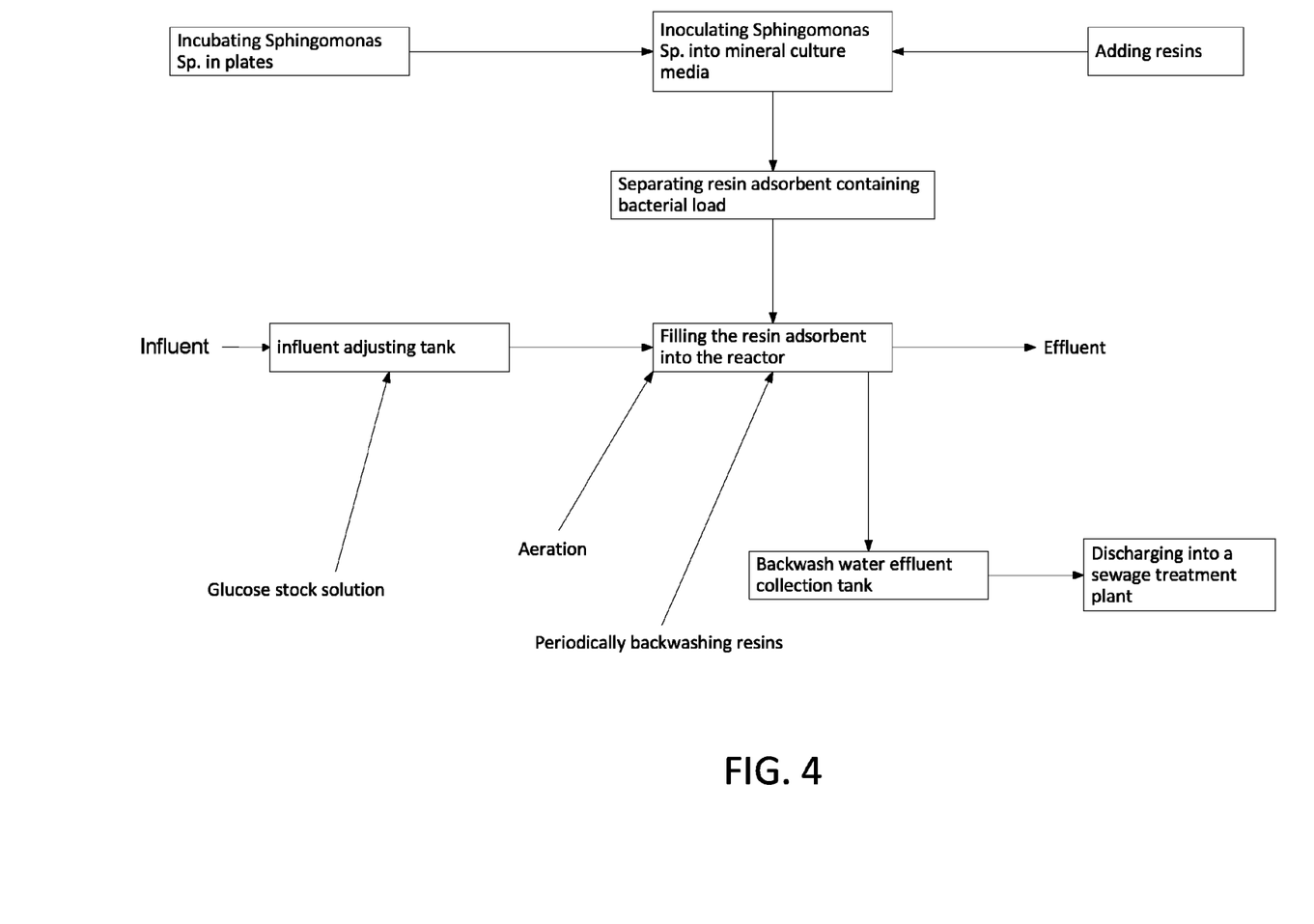

As illustrated in FIG. 4, a method for removal of tebuconazole includes the following operations.

Step 1. Providing the resins loaded with microorganisms:

(a) Culturing microorganisms (e.g., Sphingomonas paucimobilis) by: inoculating Sphingomonas bacterium colonies from plates into culture media including beef peptone and keeping the culture media from light at temperature 28 degrees Celsius;

(b) Collecting microorganisms: separating Sphingomonas paucimobilis at a logarithmic growth phase from the culture media by centrifugation for 20 min with a speed of 5000 G; washing the Sphingomonas paucimobilis using a solution (pH=7.3) containing disodium hydrogen phosphate and potassium dihydrogen phosphate;

(c) Loading the microorganisms to the resins: placing the collected microorganisms into culture media containing minerals, adding the polystyrene resins to the culture media containing minerals and shaking the culture media containing minerals for 3-5 days to obtain the resins loaded with microorganisms;

(d) Filling in the resins: washing the resins loaded with microorganisms using deionized water and filling the resins into the double honeycomb support frame of the duplex reactor.

Step 2. Adding water: adjusting water flow and flow of the complementary nutrient solution (e.g., methanol solution), controlling the inlet water sample adjustment tank such that CODCr of water samples is of 25±5 mg/L, wherein tebuconazole concentration was 4.0±0.5 mg/L, allowing the water samples into the inlet pipe of the duplex reactor, and opening the aeration pump.

Step 3. Adsorption and bio-degradation of tebuconazole: allowing the water samples pass through multiple layers of the resins, removing tebuconazole by the resins, discharging adsorption of water from the outlet pipe, wherein, at the same time, microorganisms attached to the resins uses complementary nutrients and tebuconazole as a carbon source to degrade tebuconazole, the water samples were placed in the duplex reactor for about 30 minutes, CODCr in water samples was not greater than 15 mg/L, and the tebuconazole concentration was not greater than 0.1 mg/L.

Step 4. Backwash: 7 days after the bio-degradation, due to the situation that attached microorganisms metabolism on the resins result in death and loss of certain microorganisms, closing the feed line pumps, valves and outlet valves, opening valves of the backwash water inlet and the backwash water outlet pipe, backwashing the resins for about two minutes, placing the backwash water into the backwash water effluent collection tank, discharging the backwash water into a sewage treatment plant, closing the valves of the backwash water inlet pipe and backwash water inlet outlet pipe, opening the valve and the pump of the inlet water pipeline, the water inlet valve, and continuing to run operations.

Operating Results of Example 1

| | Running time (days) | | | | | | |
|---|---|---|---|---|---|---|---|
| | 1 | 2 | 3 | 4 | 5 | 6 | 7 |
| Influent CODCr (mg/L) | 25 | 28 | 27 | 23 | 29 | 21 | 27 |
| tebuconazole concentration (mg/L) in the influent | 3.7 | 3.9 | 4.2 | 3.7 | 4.4 | 4.5 | 4.3 |
| CODCr (mg/L) in effluent | 8 | 12 | 11 | 9 | 15 | 14 | 13 |
| tebuconazole concentration (mg/L) in the effluent | 0.05 | 0.07 | 0.08 | 0.09 | 0.07 | 0.08 | 0.10 |

Example 2

The processing system is used in Example 1.

Step 1. Providing the resins loaded with microorganisms:

(a) Culturing microorganisms (e.g., Sphingomonas paucimobilis) by: inoculating microorganism colonies from plates into culture media including beef peptone and keeping the culture media from light, at temperature 28 degrees Celsius;

(b) Collecting microorganisms: separating the microorganisms at a logarithmic growth phase from the culture media by centrifugation for 20 min with a speed of 5000 G, washing the microorganisms using a solution (pH=7.3) containing disodium hydrogen phosphate and potassium dihydrogen phosphate;

(c) Loading the microorganisms to the resins: placing the collected microorganisms into culture media containing minerals, adding the polyacrylate resins to the culture media containing minerals and shaking the culture media containing minerals for 4 days to obtain the resins loaded with microorganisms;

(d) Filling in the resins: washing the resins loaded with the microorganisms using deionized water, and filling the resins into the double honeycomb support frame of the duplex reactor.

Step 2. Adding water: adjusting water flow and flow of the complementary nutrient solution (e.g., glucose solution), controlling the inlet water sample adjustment tank such that CODCr of water samples is of 40±5 mg/L, wherein tebuconazole concentration was 10.0±0.5 mg/L, allowing the water samples into the inlet pipe of the duplex reactor, and opening the aeration pump.

Step 3. Adsorption and bio-degradation of tebuconazole: allowing the water samples pass through multiple layers of the resins, removing tebuconazole by the resin, discharging adsorption of water from the outlet pipe, wherein, at the same time, microorganisms attached to the resins use complementary nutrients and tebuconazole a carbon source to degrade tebuconazole, and the water samples were placed in the duplex reactor for about 50 minutes, CODCr in water samples was not greater than 20 mg/L, and the tebuconazole concentration was not greater than 0.2 mg/L.

Step 4. Backwash: 8 days after the bio-degradation, due to the situations that attached microorganisms metabolism on the resins result in death and loss of certain microorganisms, closing the feed line pumps, valves and outlet valves, opening valves of the backwash water inlet and the backwash water outlet pipe, backwashing the resins for about three minutes, placing the backwash water into the backwash water effluent collection tank, discharging the backwash water into a sewage treatment plant, closing the valves of the backwash water inlet pipe and backwash water inlet outlet pipe, opening the valve and the pump of the inlet water pipeline, the water inlet valve, and continuing to run operations.

Operating Results of Example 2

|  | Running time (days) | | | | | | | |
| --- | --- | --- | --- | --- | --- | --- | --- | --- |
|  | 1 | 2 | 3 | 4 | 5 | 6 | 7 | 8 |
| Influent CODCr (mg/L) | 45 | 38 | 37 | 43 | 39 | 41 | 44 | 42 |
| tebuconazole concentration (mg/L) in the influent | 9.7 | 9.9 | 10.2 | 9.8 | 10.4 | 10.5 | 10..3 | 10.1 |
| CODCr (mg/L) in effluent | 17 | 15 | 11 | 19 | 15 | 17 | 20 | 15 |
| tebuconazole concentration (mg/L) in the effluent | 0.15 | 0.17 | 0.10 | 0.19 | 0.20 | 0.11 | 0.14 | 0.16 |

Example 3

The processing system is used in Example 1.

Step 1. Providing the resins loaded with microorganisms:

(a) Culturing microorganisms (e.g., *Sphingomonas paucimobilis*) by: inoculating microorganism colonies from plates into culture media including beef peptone and keeping the culture media from light at temperature 28 degrees Celsius;

(b) Collecting microorganisms: separating the microorganisms at a logarithmic growth phase from the culture media by centrifugation for 20 min with a speed of 5000 G, washing the microorganisms using a solution (pH=7.3) containing disodium hydrogen phosphate and potassium dihydrogen phosphate;

(c) Loading the microorganisms to the resins: placing the collected microorganisms into culture media containing minerals, adding the polystyrene resins to the culture media containing minerals and shaking the culture media containing minerals for 5 days to obtain the resins loaded with microorganisms;

(d) Filling in the resins: washing the resins loaded with microorganisms using deionized water, and filling the resins into the double honeycomb support frame of the duplex reactor.

Step 2. Adding water: adjusting water flow and flow of the complementary nutrient solution (e.g., sodium acetate solution), controlling the inlet water sample adjustment tank such that CODCr of water samples is of 60±5 mg/L, wherein tebuconazole concentration was 20.0±0.5 mg/L, allowing the water samples into the inlet pipe of the duplex reactor, and opening the aeration pump.

Step 3. Adsorption and bio-degradation of tebuconazole: allowing the water samples pass through multiple layers of the resins, removing tebuconazole by the resin, discharging adsorption of water from the outlet pipe, wherein, at the same time, microorganisms attached to the resins use complementary nutrients and tebuconazole as a carbon source to degrade tebuconazole, and the water samples were placed in the duplex reactor for about 80 minutes, CODCr in water samples was not greater than 25 mg/L, and the tebuconazole concentration was not greater than 0.3 mg/L.

Step 4. Backwash: 10 days after the bio-degradation, due to the situation that attached microorganisms metabolism on the resins result in death and loss of certain microorganisms, closing the feed line pumps, valves and outlet valves, opening valves of the backwash water inlet and the backwash water outlet pipe, backwashing the resins for about five minutes, placing the backwash water into the backwash water effluent collection tank, discharging the backwash water into a sewage treatment plant, closing the valves of the backwash water inlet pipe and backwash water inlet outlet pipe, opening the valve and the pump of the inlet water pipeline, and the water inlet valve, and continuing to run.

Operating Results of Example 3

|  | Running time (days) | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Influent CODCr (mg/L) | 64 | 57 | 59 | 61 | 65 | 64 | 60 | 58 | 57 | 63 |
| tebuconazole concentration (mg/L) in the influent | 20.4 | 19.8 | 19.6 | 20.3 | 20.0 | 20.1 | 20.5 | 20.4 | 20.2 | 19.9 |
| CODCr (mg/L) in effluent | 19 | 21 | 23 | 19 | 25 | 22 | 23 | 15 | 18 | 24 |
| tebuconazole concentration (mg/L) in the effluent | 0.21 | 0.19 | 0.18 | 0.24 | 0.27 | 0.23 | 0.30 | 0.26 | 0.29 | 0.30 |

Example 4

The processing system is used in Example 1.

Step 1. Providing the resins loaded with microorganisms:

(a) Culturing microorganisms (e.g., *Sphingomonas paucimobilis*): inoculating microorganism colonies from plates into culture media including beef peptone and keeping the culture media from light, at temperature 28 degrees Celsius;

(b) Collecting microorganisms: separating the microorganisms a logarithmic growth phase from the culture media by centrifugation for 20 min with a speed of 5000 G. washing the microorganisms using a solution (pH=7.3) containing disodium hydrogen phosphate and potassium dihydrogen phosphate;

(c) Loading the resins: placing the collected bacteria into culture media containing minerals, adding the polyacrylate resins to the culture media containing minerals and shaking the culture media containing minerals for 4 days to obtain the resins loaded with microorganisms;

(d) Filling in the resins: washing the resins loaded with microorganisms

5. A method using the duplex reactor of claim 4, the method comprising:
providing the resins loaded with microorganisms by:
(a) inoculating *Sphingomonas paucimobilis* colonies from plates into culture media including beef peptone, and keeping culture media from light at temperature 28 degrees Celsius,
(b) collecting *Sphingomonas paucimobilis* by separating the *Sphingomonas paucimobilis* at a logarithmic growth phase from the culture media by centrifugation and washing the *Sphingomonas paucimobilis* using a solution containing disodium hydrogen phosphate and potassium dihydrogen phosphate,
(c) loading the resins by placing the collected bacteria into culture media containing minerals, adding the resins to the culture media containing minerals, and shaking the culture media containing minerals for 3-5 days to obtain the resins loaded with microorganisms, and
(d) washing the resins loaded with microorganisms using deionized water and filling the resins into the honeycomb support frame of the duplex reactor;
adding water by adjusting water flow and flow of a complementary nutrient solution, controlling the inlet water sample adjustment tank such that CODCr of water samples is not less than 20 mg/L, allowing the water samples into the inlet pipe of the duplex reactor, and opening the aeration pump;
performing adsorption and bio-degradation of tebuconazole by allowing the water samples pass through the resins, removing tebuconazole from the resins, discharging adsorption of water from the outlet pipe such that the microorganisms are attached to the resins, wherein complementary nutrients and tebuconazole are used as a carbon source by the microorganisms and are bio-degraded, and the water samples are placed in the duplex reactor for at least 30 minutes; and
performing backwashing in 7-10 days after the bio-degradation to reduce death and loss of the microorganisms attached to the resins by closing feed line pumps, valves, and outlet valves, opening valves of the backwash water inlet pipe for backwashing water and the outlet pipe for backwashing water, backwashing the resins for not less than two minutes, placing the backwash water into the backwash water effluent collection tank, discharging the backwash water into a sewage treatment plant, closing the valves of the inlet pipe for backwashing water and the backwash water inlet outlet pipe for backwashing water, and opening the valve and the pump of an inlet water pipeline, and a water inlet valve to continue operations.

6. The method of claim 4, wherein the resins are adsorption resins including a polystyrene backbone or a polyacrylate backbone.

7. The method of claim 4, wherein a complementary nutrient solution comprises methanol, ethanol, glucose, or a solution of sodium acetate.

8. The method of claim 4, wherein the microorganisms are at in a logarithmic growth phase and are separated from culture media by centrifugation for about 20 minutes with a speed of 5000G.

9. The method of claim 4, wherein pH of the solution containing disodium hydrogen phosphate and potassium dihydrogen phosphate is of 7.3.

* * * * *

UNITED STATES PATENT AND TRADEMARK OFFICE
CERTIFICATE OF CORRECTION

| | |
|---|---|
| PATENT NO. | : 9,879,220 B2 |
| APPLICATION NO. | : 15/114225 |
| DATED | : January 30, 2018 |
| INVENTOR(S) | : Jinnan Wang et al. |

It is certified that error appears in the above-identified patent and that said Letters Patent is hereby corrected as shown below:

On the Title Page

Item (73) at Assignee, please replace "Beijing University of Technology, Beijing (CN)" with "NANJING UNIVERSITY, Nanjing (CN); Nanjing University Yancheng Environmental Protection Technology and Engineering Research Institute, Yancheng (CN)".

Signed and Sealed this
Eleventh Day of December, 2018

Andrei Iancu
*Director of the United States Patent and Trademark Office*